United States Patent [19]

Mitchell et al.

[11] 4,001,197
[45] Jan. 4, 1977

[54] MAGNETIC SEPARATION METHOD

[75] Inventors: Ralph Mitchell, Lexington; Ilan Chet, Cambridge, both of Mass.

[73] Assignee: Sala Magnetics, Inc., Cambridge, Mass.

[22] Filed: June 12, 1975

[21] Appl. No.: 586,520

[52] U.S. Cl. .......................................... 260/112 R
[51] Int. Cl.² .......................................... A23J 1/18
[58] Field of Search ................................ 260/112 R

[56] References Cited
UNITED STATES PATENTS

| | | | |
|---|---|---|---|
| 3,790,485 | 2/1974 | Sato | 260/112 R |
| 3,821,080 | 6/1974 | Kalina | 260/112 R |

*Primary Examiner*—Paul R. Michl
*Attorney, Agent, or Firm*—Joseph S. Iandiorio

[57] ABSTRACT

A magnetic separation method for recovering single cell protein from single cell organisms including dispersing magnetic seed in a fluid medium containing single cell organisms, to allow the attachment of the seed to the single cell organisms in the mixture to occur; submitting the resulting mixture to a magnetic separator to attract and hold by magnetic forces the seed and attached single cell organisms to concentrate the single cell organisms in the magnetic separator; lysing the entrapped single cell organisms to break the cell walls of the single cell organisms and release protein from the single cell organisms into the fluid medium; and recovering the released protein by discharging the fluid medium from the magnetic separator while the seed and remaining portions of the cells attached to the magnetic seed are held by the magnetic forces.

14 Claims, 4 Drawing Figures

4,001,197

MAGNETIC SEPARATION METHOD

FIELD OF INVENTION

This invention relates to a magnetic separation method for concentration and extraction of single cell protein from single cell organisms, and more particularly to such a method which concentrates the single cell organisms in a fluid medium and separates the essential single cell protein from the single cell organisms.

BACKGROUND OF INVENTION

Presently much effort is being expanded to find and develop sources of inexpensive high quality protein. One such source is single cell protein derived from single cell organisms such as bacteria, yeast, fungi and algae, which typically are available from production wastes of brewing, distilling and fermentation processes and which can be grown on such diverse substrates as, e.g., sewage, petroleum, garbage, paper, dairy and food industry wastes. Major costs in the recovery of single cell protein from these and other growth environments is the separation or concentration first, of the single cell organisms from the fluid medium in which they are grown and second, the subsequent separation of the single cell protein from unusable portions of the cell. Conventional separation techniques such as centrifugation, filtration and flocculation-sedimentation have met with indifferent success solving these two problems. In each of these techniques the single cell organisms are first concentrated in the filter or centrifuge and then removed from there for subsequent extraction of useful protein. A second filtration or centrifugation is then necessary to separate the useable protein from the unuseable portions of the cells. More specifically the filtration technique suffers from rapid filter clogging necessitating frequent filter cleanings and replacements. Centrifugation is a slow process requiring complex equipment which must be carefully adjusted for optimum production and which requires large power inputs. Flocculation-sedimentation requires the addition of flocculant chemicals which may be toxic and difficult subsequently to separate from the single cell organisms or useful protein. This technique also results in large volumes of water being recovered with the single cell organisms or the useful protein which are only eliminated at additional expense.

SUMMARY OF INVENTION

It is therefore an object of this invention to provide an improved, simple, inexpensive, and extremely effective magnetic separation method for both separation steps: concentrating the single cell organisms and recovering high quality single cell protein from the concentrated single cell organisms.

The invention results from the realization that concentration of single cell organisms and recovery of the single cell protein from the concentrated single cell organisms can each be accomplished using a magnetic separation method in the same or separate operations of a magnetic separator.

The invention features a magnetic separation method for recovering single cell protein from a fluid medium containing single cell organisms. Magnetic seed is dispersed in a fluid medium containing single cell organisms to allow the attachment of the magnetic seed to the single cell organisms to occur. That mixture is submitted to a magnetic separator which entraps and holds the magnetic seed and attached single cell organisms in the separator under the influence of the magnetic forces. The single cell organisms are concentrated, in this way, in the magnetic separator. The entrapped single cell organisms held in the separator by the interaction of the magnetic seed and the magnetic forces provided in the magnetic separator are then lysed to break the cell walls of the single cell organisms and release protein from the single cell organisms into the fluid medium. The recovery of the protein released into the fluid medium is accomplished by discharging the fluid medium containing the protein from the magnetic separator while the seed and remaining unuseable portions of the single cell organisms are held by magnetic forces in the magnetic separator.

In preferred embodiments a binding medium may be mixed with the magnetic seed and fluid medium containing single cell organisms to improve attachment of the magnetic seed to the single cell organisms. Mixing of the fluid medium containing the magnetic seed and the single cell organisms may be carried out to enhance the attachment of the seed to the organisms. Lysing may be accomplished either within or remote from the separator using ultrasonic energy or a caustic medium.

DISCLOSURE OF PREFERRED EMBODIMENT

Other objects, features and advantages will occur from the following description of a preferred embodiment and the accompanying drawings, in which.

Figure 1:
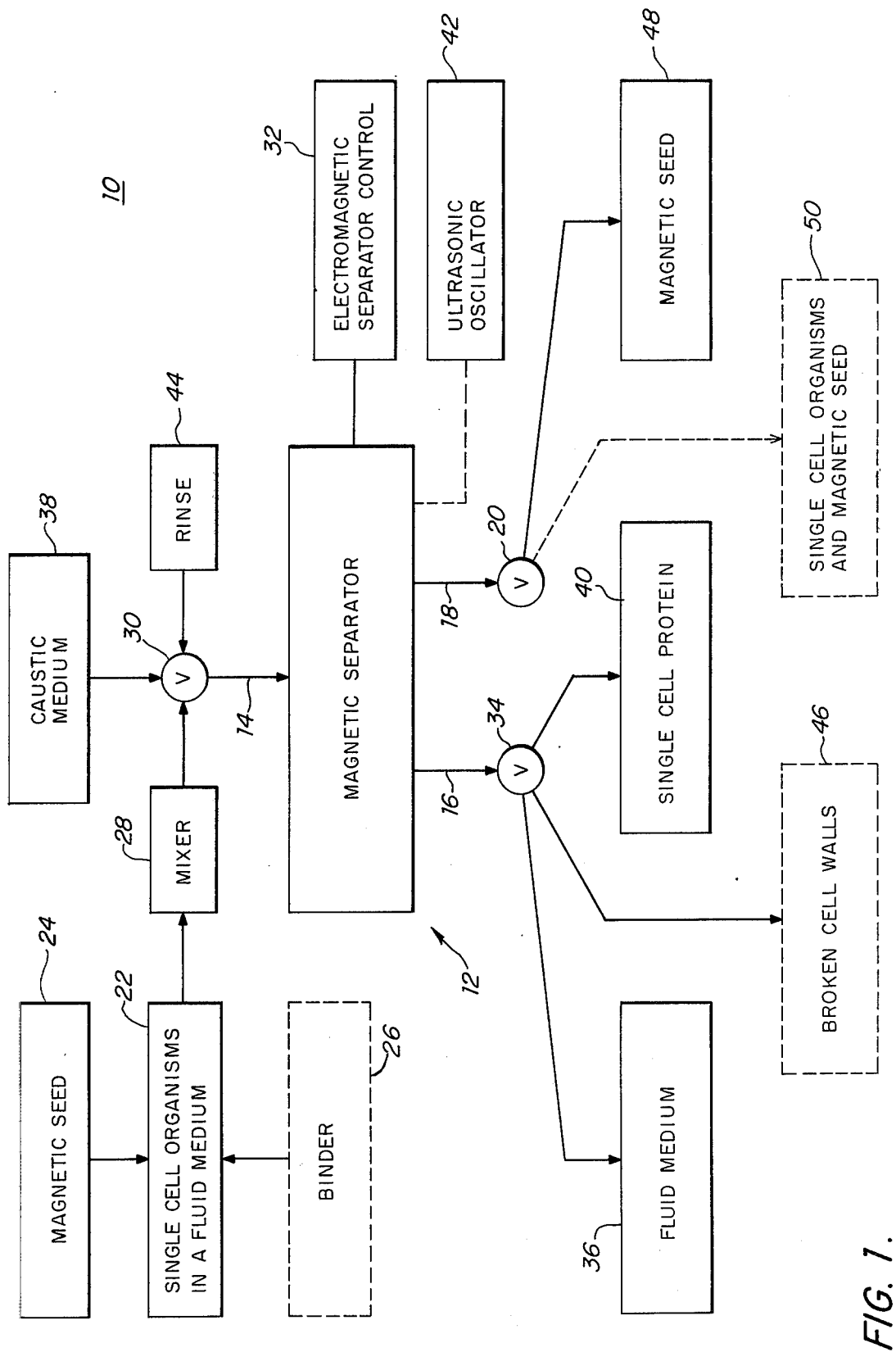
FIG. 1 is a schematic block diagram of a magnetic separation system which may be used to carry out the method of this invention.

The invention may be accomplished with a magnetic separation method for recovery of single cell protein from a fluid medium containing single cell organisms which include the steps of dispersing magnetic seed to a fluid medium containing single cell organisms. Subsequently, the mixture is submitted to a magnetic separator to entrap and hold in the separator the magnetic seed and attached single cell organisms under the influence of the magnetic forces. Then the entrapped single cell organisms are lysed to break down the walls of the single cell organisms and release protein from the single cell organisms into the fluid medium. The recovery of the protein released in the fluid medium is accomplished by discharging the fluid medium containing the protein from the magnetic separator while the seed and the remaining unuseable portions of the single cell organisms are held by magnetic forces in the magnetic separator.

The single cell organisms operated on include algae, yeast, fungi and bacteria. A binder may be used to further promote the attachment of the magnetic seed to the single cell organisms. Typically, the magnetic seed may be magnetite and the binder may be calcium chloride. With yeast cells in an aqueous solution of $10^7$ cells per ml, 2000 ppm of magnetite and 100 ppm of calcium chloride is used. Lysing may be accomplished using either a caustic medium such as 0.2 molar sodium hydroxide or by using ultrasonic vibrations to break the cell walls.

If it is desirable to recover the magnetic seed, after lysing has been accomplished, a stronger caustic medium such as 1 molar sodium hydroxide may be introduced into the magnetic separator to further break down the cell walls of the single cell organisms and separate the remaining portions of the single cell organisms from the magnetic separator. Subsequently reducing the magnetic field strength releases the seed which can be discharged from the magnetic separator and recovered. In addition, in the seed recovery operation the magnetic field strength may be increased during the introduction of the stronger caustic medium and the stronger caustic medium itself may be introduced at higher velocity to increase the differential forces applied to the magnetic seed and the associated remaining portions of the single cell organisms to further enhance the separation. In cases where the lysing is required to be done external to the magnetic separator the strength of the magnetic forces in the magnetic separator may be decreased following the initial separation and concentration of the single cell organisms. Then the single cell organisms with the seed attached may be discharged from the magnetic separator in a small volume of fluid. Following this the single cell organisms may be lysed to break the cell walls of the single cell organisms and release protein from the remainder of the cell and attached magnetic seed. Finally, this lysed mixture containing the released protein and the remaining portions of the cell with the attached magnetic seed is resubmitted to a magnetic separator which will entrap and hold the magnetic seed and attached remaining portions of the cell under the influence of the magnetic forces, while allowing the released protein and the fluid medium to pass through the magnetic separator and be recovered.

There is shown in FIG. 1 a magnetic separation system 10 which may be used to implement the magnetic separation method of this invention. System 10 includes a magnetic separator 12 including an inlet 14 for feeding a fluid to the separator and outlets 16 and 18 for discharging non-magnetic 16 and magnetic 18 components of the feed. Several types of magnetic separators may be used in the method disclosed here. For example, cyclic or continuous matrix type magnetic separators may be used. This type of separator is disclosed in U.S. Pat. Nos. 3,627,678; 3,770,629; 3,887,457; 3,676,337; and 3,567,026. In this description of the method disclosed here reference will be made to cyclic type magnetic separators in which the feed to be separated is passed intermittantly to the magnetic separator and the non-magnetic and magnetic components are discharged at alternate times. It is understood that many continuously operating magnetic separators are capable of reproducing the operations described here on a continuous rather than sequential basis and may also be used in the method disclosed here. Magnetic seed and binder from sources 24 and 26, respectively, are dispersed in fluid medium 22 containing single cell organisms. This mixture may be delivered to mixer 28 where they are agitated to enhance attachment of the magnetic seed to the single cell organisms. In this preferred embodiment the binder from source 26 is used to further promote attachment. Mixer 28 may be a device such as a New Brunswick rotary shaker. From mixer 28, the mixture including the single cell organisms in the fluid medium and the magnetic seed, and if appropriate, the binder, is fed through valve 30 into the feed inlet 14 of the magnetic separator, while magnetic separator 12 is energized by the electromagnetic separator control 32 to effect a magnetic separation which enables the non-magnetic fluid medium with the single cell organisms removed to pass out from the magnetic separator through outlet 16 and into collector 36.

Valve 30 is now operated to cut off the flow from the mixer 28 and introduce a caustic medium from source 38 to the magnetic separator 12 where it lyses or breaks apart the single cell organisms, trapped within the separator leaving the broken cell walls with the magnetic seed attached entrapped in the magnetic separator 12 by the magnetic forces and permits passage out of separator 12 through non-magnetic outlet 16 of the single cell protein which is delivered by valve 34 to collector 40. Alternatively, the lysing may be accomplished using an ultrasonic oscillator 42 such as a Branson ultrasonic disintegrator which vibrates matrix 18 at a ultrasonic frequency of 8,000 KHz per second to break the cell walls of the single cell organisms and free the single cell protein. In this case a small amount of rinse fluid from source 44 is introduced through valve 30 to effect the discharge of the released protein.

Following lysing accomplished in either of these ways, recovery of the magnetic seed may be accomplished by adding a stronger caustic medium through valve 30 to remove the broken cell walls from the magnetic seed. In this operation the magnetic forces in the magnetic separator may be increased by the electromagnetic separator control and the stronger caustic medium may be passed through the separator at higher velocity in order to increase the differential force between the broken cell walls and the magnetic seed. The broken cell walls are delivered through the non-magnetic outlet 16 by valve 34 to collector 46 subsequent to which the magnetic separator is deenergized by the electromagnetic separator control 32 and a small amount of rinse fluid is delivered from source 44 to valve 30 to wash out the magnetic seed through the magnetic outlet 18 and valve 20 to the magnetic seed collector 48.

Alternatively, if it is desired to perform the lysing operation external to magnetic separator 12, the magnetic separator may be deenergized by electromagnetic separator control 32 immediately after the separation and before any lysing has taken place. During this deenergization period, with the aid of a rinse fluid from source 34, the single cell organisms and attached magnetic seed may be delivered through the magnetic outlet 18 and valve 20 to collector 50, shown in phantom. Lysing is then accomplished either in collector 50 or at some other site. The broken cell walls of the single cell organisms, the released single cell protein, and the magnetic seed are then resubmitted to a magnetic separator; typically, a separator, like separator 12, provided with suitable interconnections and valving is used for the second separation as well as the first. With the magnetic separator energized the broken cell walls and magnetic seed are entrapped in the separator 12 while the released single cell protein is passed through and discharged by the non-magnetic outlet 16 and may be delivered through valve 34 to a collection point such as collector 40. The broken cell walls and magnetic seed may then be dealt with as previously discussed.

The method disclosed here may also be accomplished by using a continuous type of magnetic separator. It will be recognized by those skilled in the art of magnetic separation that with external plumbing suitably arranged above, the operations which are classified as sequential in time may be carried out sequentially in space in the operation of a continuous magnetic separator.

In particular in a continuous magnetic separation device separate feed lines to different parts of the separator would be used to deliver the initial seed mixture, caustic medium and rinse and similarly separate outlets for all the magnetic and non-magnetic products would exist eliminating the need for the valves 30, 34 and 20, indicated in FIG. 1.

Figure 2:
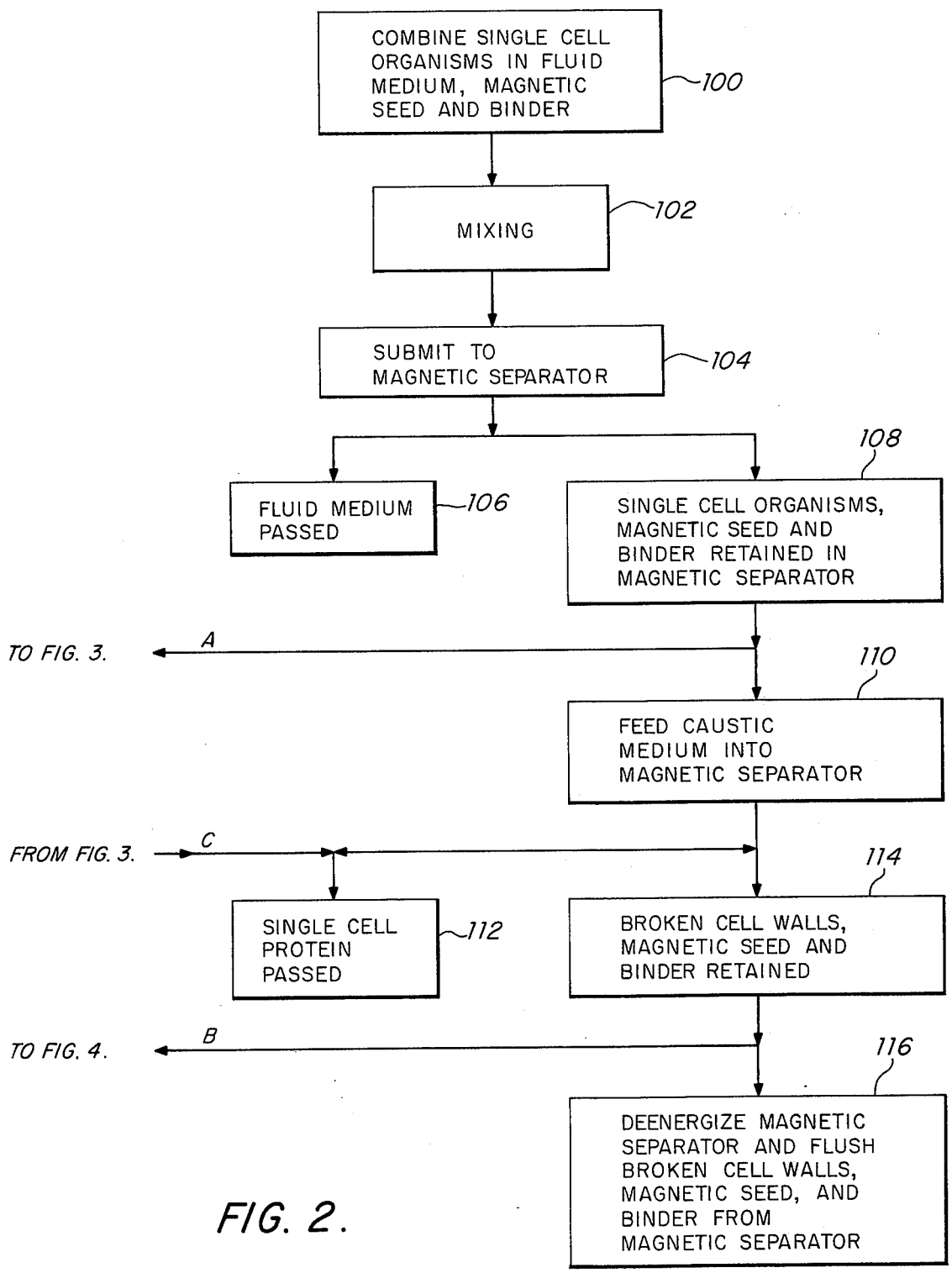
FIG. 2 is a flow chart illustrating the magnetic separation method according to this invention.
Figure 3:
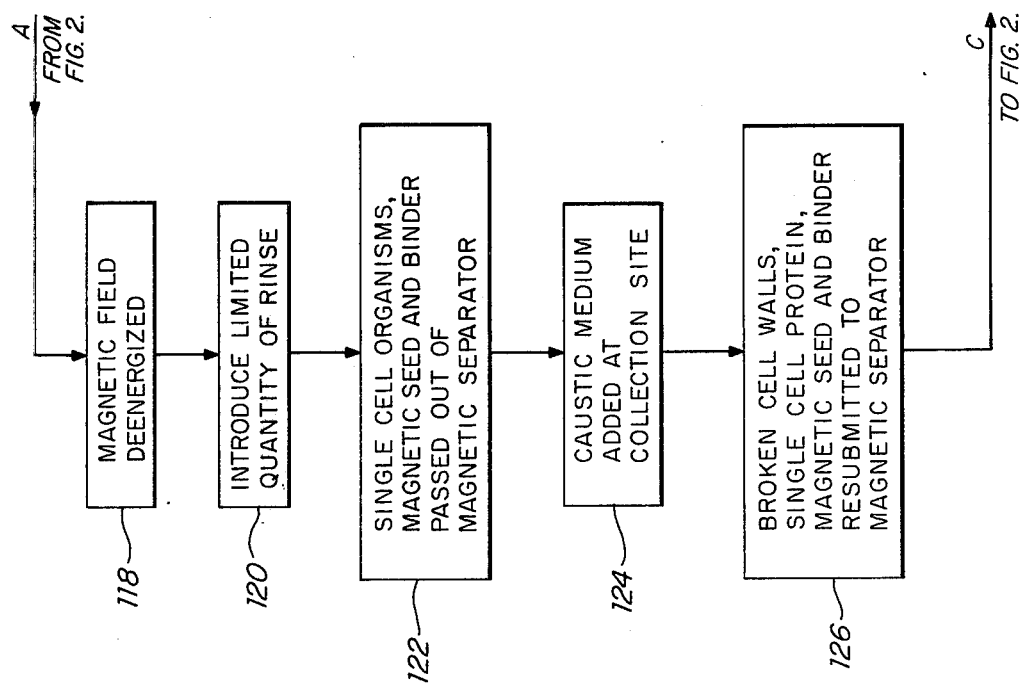
FIG. 3 is a flow chart of an alternative embodiment of the magnetic separation method of this invention in which the lysing is accomplished external to a magnetic separator.

In execution the method of this invention, illustrated in FIG. 2, includes combining single cell organisms in fluid media with magnetic seed and, if desired, a binder 100, then mixing 102, if desired, these components to enhance attachment of the magnetic seed to the single cell organisms. Following this the mixture is submitted 104 to a magnetic separator such as shown in FIG. 1. The fluid medium which has been acting as the vehicle for the single cell organism is passed 106 and the single cell organisms, the magnetic seed and the binder are retained 108 by the magnetic forces in the magnetic separator. If lysing is to be accomplished external to the magnetic separator, path A, illustrated in FIG. 3, is executed next. If, however, lysing is to take place in the magnetic separator then caustic medium is fed 110 into the magnetic separator following which the single cell protein is discharged 112 from the separator and the broken cell walls with the magnetic seed and binder are retained 114 in the magnetic separator. If the magnetic seed is to be recovered, path B, illustrated in FIG. 4, is followed; if not then the magnetic separator is deenergized and the broken cell walls, magnetic seed and binder are flushed from the magnetic separator 116.

External lysing, path A, is realised by deenergizing the magnetic separator 118, FIG. 3, then introducing 120 a limited quantity of rinse fluid to the separator. Following this the single cell organisms, magnetic seed and binder are discharged 122 from the separator to some collection site. At the collection site a caustic medium is added 124 to lyse the single cell organisms. This yields broken cell walls, single cell protein, magnetic seed and binder all of which are resubmitted 126 to the same or a second magnetic separator along path C, FIG. 2, to undergo steps 112, 114 and 116 or the steps of path B as before.

Figure 4:
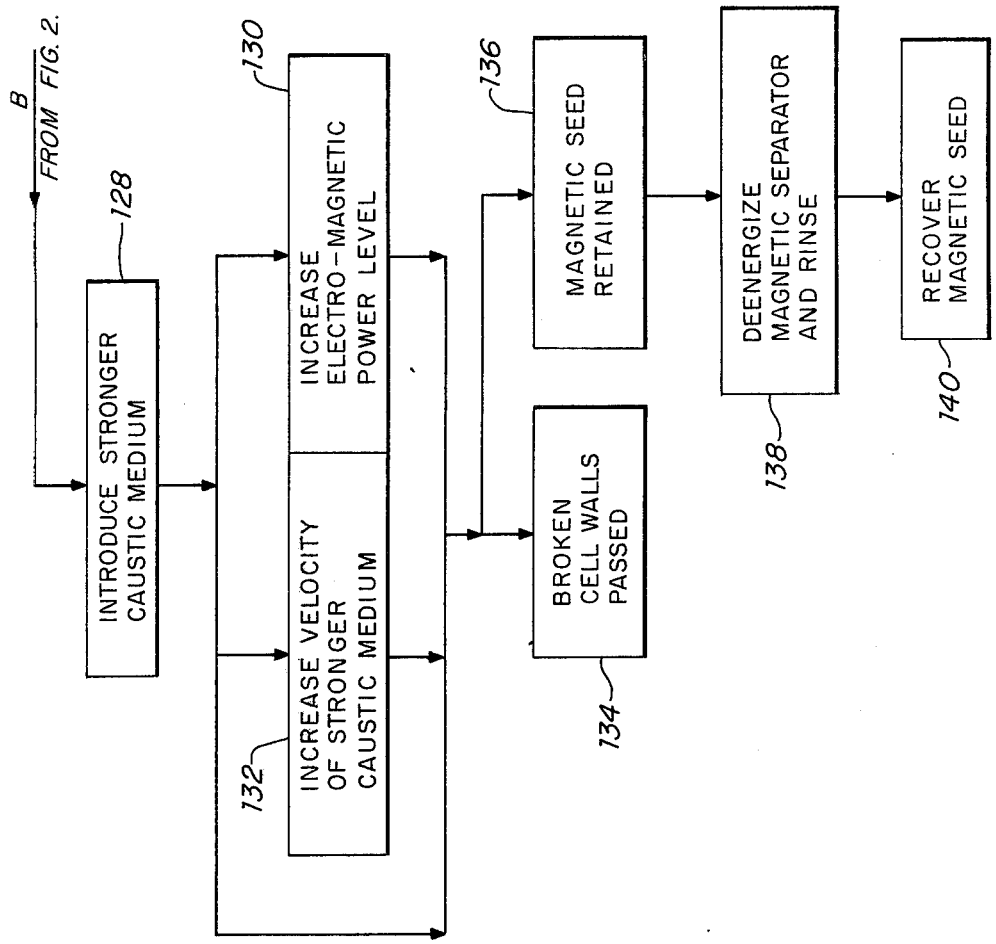
FIG. 4 is a flow chart which extends the magnetic separation method of this invention to recovery of the magnetic seed.

Path B, FIG. 4, illustrates the seed recovery technique which may be accomplished with the method of this invention. Following the separation of the single cell protein from the broken cell walls, magnetic seed and binder in steps 112 and 114 in FIG. 2 a stronger caustic medium may be introduced 128 to the magnetic separator to separate the broken cell walls from the magnetic seed. During this operation the electro-magnetic separator power level may be increased 130 and the velocity of the stronger caustic medium through the separator may be increased 132 to increase the differential in the forces between the magnetic seed and the broken cell walls. The broken cell walls are discharged 134 out of the separator while the magnetic seed is retained 136. The magnetic separator is then deenergized 138 and a rinse removes the magnetic seed from the separator for recovery 140.

Other embodiments will occur to those skilled in the art and are within the following claims:

What is claimed is:

1. A magnetic separation method for recovering single cell protein from single cell organisms comprising:
    dispersing magnetic seed in a fluid medium containing single cell organisms, to allow attachment of the magnetic seed to the single cell organisms in the mixture to occur;
    submitting the mixture to a magnetic separator to entrap and hold by magnetic forces in the magnetic separator the magnetic seed and attached single cell organisms, to concentrate the single cell organisms;
    lysing the entrapped single cell organisms to break the cell walls of the single cell organisms and release protein from the single cell organisms into the fluid medium; and
    recovering the released protein in the fluid medium by discharging the fluid medium from the magnetic separator while the seed and remaining portions of the cells which are attached to the magnetic seed are held by the magnetic forces.

2. The magnetic separation method of claim 1 further including adding a step of mixing the magnetic seed and a single cell organism mixture to enhance attachment of the magnetic seed to the single cell organisms.

3. The magnetic separation method of claim 1 further including adding a binding medium with the magnetic seed to the fluid medium containing single cell organisms to improve attachment of the magnetic seed to the single cell organisms.

4. The magnetic separation method of claim 1 in which the lysing is performed by introducing a caustic medium into the magnetic separator to break the cell walls of the single cell organisms.

5. The magnetic separation method of claim 1 in which the lysing is performed by subjecting the single cell organisms in the magnetic separator to ultrasonic energy to break the cell walls of the single cell organisms.

6. The magnetic separation method of claim 1 further including:
    introducing to the magnetic separator, after lysing has been accomplished, a stronger caustic medium for further breaking down the cell walls of the single cell organisms to separate the remaining portions of the single cell organisms from the magnetic seed; and
    reducing the magnetic forces in the magnetic separator to release the seed.

7. The magnetic separation method of claim 5 in which the strength of the magnetic forces are increased during the introduction of the stronger caustic medium and the stronger caustic medium is passed through the magnetic separator at an increased velocity to increase the differential of the forces applied to the magnetic seed and the associated remaining portions of the single cell organisms.

8. A magnetic separation method for recovering single cell protein from single cell organisms comprising:
    dispersing magnetic seed in a fluid medium containing single cell organisms to allow attachment of the magnetic seed to the single cell organisms in the mixture to occur;
    submitting the mixture to a magnetic separator to entrap and hold, by magnetic forces, in the magnetic separator the magnetic seed and attached single cell organisms, to concentrate the single cell organisms;

decreasing the strength of the magnetic forces;

washing the single cell organisms with seed attached from the magnetic separator using a small volume of fluid;

lysing the single cell organisms to break the cell walls of the single cell organisms and release protein from the single cell organisms into the fluid medium; and resubmitting the lysed mixture containing the released protein and the remainders of the single cell organisms with attached magnetic seed to a magnetic separator to entrap and hold, in the magnetic separator by magnetic forces, the magnetic seed and attached remainders of the single cell organisms and to pass and recover the released protein.

9. The magnetic separation method of claim 8 further including adding a step of mixing the magnetic seed and single cell organism mixture to enhance attachment of the magnetic seed to the single cell organism.

10. The magnetic separation method of claim 8 further including adding a binding medium with the magnetic seed to the fluid medium containing single cell organisms to improve attachment of the magnetic seed to the single cell organisms.

11. The magnetic separation method of claim 8 in which the lysing is performed by introducing a caustic medium into the magnetic separator to break the cell walls of the single cell organisms.

12. The magnetic separation method of claim 8 in which the lysing is performed by subjecting the single cell organisms in the magnetic separator to ultrasonic energy to break the cell walls of the single cell organisms.

13. The magnetic separation method of claim 1 further including:

introducing to the magnetic separator, after lysing has been accomplished, a stronger caustic medium for further breaking down the cell walls of the single cell organisms to separate the remaining portions of the single cell organisms from the magnetic seed; and reducing the magnetic forces in the magnetic separation to release the seed.

14. The magnetic separation method of claim 13 in which strength of the magnetic field is increased during the introduction of the stronger caustic medium and the stronger caustic medium is passed through the magnetic separator at an increased velocity to increase the differential of the forces applied to the magnetic seed and the associated remaining portions of the single cell organisms.

* * * * *